United States Patent [19]

Hayami et al.

[11] Patent Number: 4,530,797

[45] Date of Patent: Jul. 23, 1985

[54] PROCESS FOR PRODUCING POLYCHLOROBENZONITRILE

[75] Inventors: Hiroshi Hayami, Takasaki; Yasuo Kuroda, Gunma; Makoto Kikuchi, Takasaki; Kenji Koshi, Fukuyama, all of Japan

[73] Assignee: Nippon Kayaku Kabushiki Kaisha, Tokyo, Japan

[21] Appl. No.: 648,745

[22] Filed: Sep. 10, 1984

[51] Int. Cl.$^3$ ............................................. C07C 120/14
[52] U.S. Cl. ............................. 260/465 C; 260/465 G
[58] Field of Search ..................................... 260/465 C

[56] References Cited

U.S. PATENT DOCUMENTS

| | | | |
|---|---|---|---|
| 3,399,225 | 8/1968 | Tarama et al. | 260/465 C |
| 4,010,188 | 3/1977 | Grasselli et al. | 260/465 C |
| 4,124,631 | 11/1978 | Hayami et al. | 260/465 C |

Primary Examiner—Dolph H. Torrence
Attorney, Agent, or Firm—Henry C. Nields

[57] ABSTRACT

A process for producing polychlorobenzonitrile having chlorine atoms at the 2,6-position by ammoxidation of toluene derivative having chlorine atoms at the 2,6-position with a gas containing ammonia and oxygen in vapor phase in the presence of a catalyst, characterized in that bromine and/or a bromine-containing compound is added to the reaction system.

8 Claims, No Drawings

PROCESS FOR PRODUCING POLYCHLOROBENZONITRILE

DETAILED DESCRIPTION OF THE INVENTION

The present invention relates to a process for producing polychlorobenzonitrile having chlorine atoms at the 2,6-position by ammoxidation of toluene derivative having chlorine atoms at the 2,6-position with a gas containing ammonia and oxygen in vapour phase in the presence of a catalyst, characterized in that bromine and/or a bromine-containing compound is added to the reaction system.

The toluene derivative having chlorine atoms at the 2,6-position (abbreviated as 2,6-DCT hereinafter) include, for example, 2,6-dichlorotoluene, 2,3,6-trichlorotoluene, and 2,4,6-trichlorotoluene. According to the process of this invention, they are converted into 2,6-dichlorobenzonitrile, 2,3,6-trichlorobenzonitrile, and 2,4,6-trichlorobenzonitrile, respectively.

2,6-Dichlorobenzonitrile which is obtained by ammoxidation of 2,6-dichlorotoluene is an effective weed killer per se, and it is also an important intermediate for agricultural chemicals and medicines. And recently there is an increasing demand for this compound. At present, this compound is synthesized through a very complex route, and it is hoped that an economical process will be developed.

Heretofore, there have been proposed several processes for producing 2,6-dichlorobenzonitrile by ammoxidation of 2,6-dichlorotoluene. The ammoxidation of 2,6-dichlorotoluene has a disadvantage in that it is necessary to use oxygen and ammonia in large excess and to extend the reaction time, because the methyl group to be oxidized is less active than that in other aromatic methyl compounds due to the presence of bulky chlorine atoms at the both ortho positions. The maximum yield attained so far was 79%. (Japanese Patent Publication No. 7902/1967).

The present inventors performed extensive studies on the improvement of yield and productivity in the production of polychlorobenzonitrile (abbreviated as 2,6-DCBN hereinafter), having chlorine atoms at the 2,6-position as the substituents, by ammoxidation of 2,6-DCT. As the result, it was found that the ammoxidation of 2,6-DCT is improved in yield and performance regardless of the kind of catalyst system used and it is not necessary to use oxygen and ammonia in large excess, if bromine and/or a bromine-containing compound is added to the reaction system. The present invention was completed based on this finding.

The process of this invention provides better yields than the conventional process in which a bromine compound is not added, regardless of the kind of catalyst system used. However, it is preferred to use a high-performance catalyst system for the production of 2,6-DCBN. Examples of such catalyst system include V-Fe catalyst as disclosed in Japanese Patent Publication No. 7902/1967, V catalyst and V-Cr catalyst as disclosed in Japanese Patent Publication No. 10623/1968, and V-P catalyst as disclosed in Japanese Patent Laid-open No. 121738/1978 and U.S. Pat. No. 4,124,631.

To be concrete, the preferred catalyst is one which has the following composition.

$$V_1Fe_xO_y \qquad (1)$$

wherein x and y denote the atomic ratio of iron and oxygen, x being 0.5 to 10 and y being a value which is determined according to the valence and atomic ratio of other elements.

$$V_1P_aA_bO_c \qquad (2)$$

wherein A denotes at least one element selected from the group consisting of chromium, manganese, iron, cobalt, nickel, and tin; and a, b, and c denote the atomic ratio of phosphorus, A, and oxygen, respectively, a being 0.5 to 3, b being 0 to 2, and c being a value which is determined according to the valence and atomic ratio of other elements.

$$V_1Cr_xO_y \qquad (3)$$

wherein x and y denote the atomic ratio of chromium and oxygen, x being 0.1 to 3.0, and y being a value which is determined according to the valence and atomic ratio of other elements.

The scope of this invention is not restricted by these catalyst systems. Any known catalysts can be used in the process of this invention, and they can be produced according to the known processes. For example, a preferred catalyst may be produced by mixing the compounds of the constituting elements in the presence of water and evaporating the mixture to dryness, followed by calcination preferably at 400° to 650° C. The carrier such as alumina, silica, beryllia, magnesia, titania, silicon carbide, asbestos, and diatomaceous earth can be used. However, the carrier may not be required.

The bromine-containing compound used in the process of this invention includes, for example, hydrogen bromide, methyl bromide, dibromomethane, bromoform, carbon tetra-bromide, ethyl bromide, 1,2-dibromoethane, n-propyl bromide, i-propyl bromide, n-butyl bromide, i-butyl bromide, sec-butyl bromide, i-amyl bromide, sec-amyl bromide, t-amyl bromide, cyclopentyl bromide, cyclohexyl bromide, bromobenzenes, and bromotoluenes. In addition to these compounds, those bromine compounds which are a gas at the reaction temperature can be used. These bromine compounds is added in an amount of preferably 0.1 to 10 wt %, more preferably 0.3 to 5 wt %, based on the quantity of 2,6-DCT.

The reaction conditions in the process of this invention varies depending on the catalyst used. Oxygen and ammonia is used each in an amount of preferably 2 to 5 mol for 1 mol of 2,6-DCT. The reaction temperature in the process of this invention may be lower than that in other processes. The preferred reaction temperature is 330° to 450° C. The reaction can be performed under pressure, under normal pressure, or under reduced pressure. The process of this invention can be performed by using a fixed bed reactor or fluidized bed reactor.

The invention is now described in more detail with reference to the following examples and comparative examples, which should not be construed to restrict the scope of this invention. The conversion, yield, and selectivity based on 2,6-DCT are defined as follows:

· Conversion (%)=A/B×100
where
A: number of moles of reacted 2,6-DCT, and
B: number of moles of 2,6-DCT fed to the reaction zone.
Yield (%)=C/D×100 where
C: number of moles of 2,6-DCBN obtained, and
D: number of moles of 2,6-DCT fed to the reaction zone.

Selectivity (%) = E/F × 100
where
E: number of moles of 2,6-DCBN obtained, and
F: number of moles of reacted 2,6-DCT.

EXAMPLE 1

117 g of ammonium metavanadate was completely dissolved in 1 liter of water by heating. To this solution was added 139.2 g of 85% phosphoric acid to give a dark brown solution. To this solution was added 2400 ml of silica sol containing 471 g of silica, followed by heating and stirring, to give a uniform suspension. This suspension underwent spray drying to give granules. The granules were calcined at 580° C. for 5 hours to give a catalyst having the composition of $V_1P_{1.2}O_{5.5}$ ($SiO_2$ 70%).

300 g of this catalyst was placed in a fluidized bed reactor, 1.5 inches in inside diameter and 100 cm high, and was heated therein at 360° C. To this catalyst layer were fed air, 2,6-dichlorotoluene containing 2% of ethyl bromide, and ammonia at rates of 75.2 N liters, 38.2 g, and 15.7 N liters per hour, respectively. The ratio of 2,6-dichlorotoluene:oxygen:ammonia was 1:3:3. 2,6-dichlorobenzonitrile was obtained in an amount of 34.7 g per hour. The quantity of unreacted 2,6-dichlorotoluene was 0.8 g. Conversion was 97.9%, yield was 86.7%, and selectivity was 88.5%.

COMPARATIVE EXAMPLE 1

Example 1 was repeated except that ethyl bromide was not used. The quantity of 2,6-dichlorobenzonitrile obtained was 21.8 g, and the quantity of unreacted 2,6-dichlorotoluene was 11.9 g. Conversion was 68.8%, yield was 53.2%, and selectivity was 77.5%.

EXAMPLES 2 to 4

Example 1 was repeated except that the quantity of ethyl bromide mixed in 2,6-dichlorotoluene was changed from 0.5 to 3%. The results are shown in Table 1.

TABLE 1

| Example | Quantity of ethyl bromide | Conversion (%) | Yield (%) | Selectivity (%) |
|---|---|---|---|---|
| 2 | 0.5% | 89.7 | 74.0 | 82.5 |
| 3 | 1% | 96.9 | 81.6 | 84.2 |
| 4 | 3% | 98.5 | 88.2 | 89.5 |

EXAMPLES 5 to 11

Example 1 was repeated except that 2% of ethyl bromide was replaced by 2% of bromine, hydrogen bromide, bromobenzene, ethylene dibromide, i-propyl bromide, n-propyl bromide, or i-amyl bromide. The results are shown in Table 2.

TABLE 2

| Example | Additive | Conversion (%) | Yield (%) | Selectivity (%) |
|---|---|---|---|---|
| 5 | Bromine | 89.0 | 72.5 | 81.5 |
| 6 | Hydrogen bromide | 92.4 | 74.8 | 81.0 |
| 7 | Ethylene bromide | 88.0 | 76.4 | 86.2 |
| 8 | Bromo-benzene | 87.3 | 70.3 | 80.5 |
| 9 | n-Propyl bromide | 95.9 | 83.7 | 87.3 |
| 10 | i-Propyl bromide | 93.8 | 79.0 | 84.3 |
| 11 | i-Amyl bromide | 95.2 | 83.4 | 87.8 |

EXAMPLE 12

Alumina sol was made into spherical γ-alumina by spray drying. It was then calcinated at 1000° C. for 6 hours. 5.37 g of vanadium pentoxide was suspended in 30 ml of water. While keeping the suspension at 80° to 90° C., 190 g of oxalic acid [$(COOH)_2.2H_2O$] was added slowly with stirring. There was obtained a bluish solution of vanadyl oxalate. Ferric nitrate was dissolved in water to give 51 cc of aqueous solution containing 0.185 g of iron (in terms of $Fe_2O_3$) in 1 cc. The two solutions were mixed together and diluted to 104 cc with water. 300 g of the calcined alumina was impregnated with 104 cc of the mixed solution, followed by heat-drying overnight at 100° to 120° C. The impregnated alumina was calcined at 450° C. for 2 hours in an air stream. Thus there was obtained a vanadium oxide-iron oxide catalyst supported on alumina. The atomic ratio of V to Fe in the catalyst was about 1:2.

270 g of this catalyst was charged into the same fluidized bed reactor as used in Example 1. The catalyst layer was kept at 390° C. To the catalyst layer were fed air, 2,6-dichlorotoluene containing 2% of ethyl bromide, and ammonia at rates of 71.6 N liters, 25.0 g, and 17 N liters per hour, respectively. The ratio of 2,6-dichlorotoluene:oxygen:ammonia was 1.0:4.2:5.0. 2,6-dichlorobenzonitrile was obtained in an amount of 21.5 g per hour. The quantity of unreacted 2,6-dichlorotoluene was 1.6 g. Conversion was 94.5%, yield was 82.3%, and selectivity was 87.1%.

COMPARATIVE EXAMPLE 2

Example 12 was repeated except that ethyl bromide was not used. The quantity of 2,6-dichlorobenzonitrile obtained in one hour was 16.2 g, and the quantity of unreacted 2,6-dichlorotoluene was 6.0 g. Conversion was 76.0%, yield was 60.6%, and selectivity was 79.7%.

EXAMPLE 13

Example 1 was repeated except that the reaction temperature was changed to 355° C. and 2,6-dichlorotoluene containing 2% of ethyl bromide was replaced by 2,4,6-trichlorotoluene containing 2% of n-propyl bromide which was fed at a rate of 50.5 g per hour. 2,4,6-trichlorobenzonitrile was obtained in an amount of 40.7 g per hour. The quantity of unreacted 2,4,6-trichlorotoluene was 4.8 g. Conversion was 90.3%, yield was 77.9%, and selectivity was 86.3%.

COMPARATIVE EXAMPLE 3

Example 13 was repeated except that n-propyl bromide was not used. Conversion was 77.8%, yield was 60.1%, and selectivity was 77.2%.

EXAMPLE 14

Example 1 was repeated except that 2,6-dichlorotoluene containing 2% of ethyl bromide was replaced by 2,3,6-trichlorotoluene containing 3% of n-propyl bromide which was fed at a rate of 51.0 g per hour. 2,3,6-trichlorobenzonitrile was obtained in an amount of 42.2 g per hour. The quantity of unreacted 2,3,6-trichlorotoluene was 3.8 g per hour. Conversion was 92.3%, yield was 80.7%, and selectivity was 87.4%.

COMPARATIVE EXAMPLE 4

Example 14 was repeated except that n-propyl bromide was not used. Conversion was 74.5%, yield was 58.4%, and selectivity was 78.3%.

EXAMPLES 15 to 21

Ammoxidation of Example 1 was repeated except that a catalyst having the composition of $V_1P_{1.2}O_{5.5}(SiO_2 70\%)$ was replaced by the each catalyst which is listed in Table 3. The results are shown in Table 3.

TABLE 3

| Example | Catalyst | Conversion (%) | Yield (%) | Selectivity (%) |
|---|---|---|---|---|
| 15 | $V_1Cr_1O_{5.5}(\alpha\text{-}Al_2O_3 97\%)$ | 84.8 | 75.5 | 89.0 |
| 16 | $V_1P_{1.2}Cr_{0.3}O_{6.4}(SiO_2 70\%)$ | 95.5 | 81.4 | 85.2 |
| 17 | $V_1P_{1.2}Mn_{0.3}O_{6.55}(SiO_2 70\%)$ | 98.0 | 86.1 | 87.8 |
| 18 | $V_1P_{1.2}Fe_{0.3}O_{6.1}(SiO_2 70\%)$ | 96.7 | 83.4 | 86.2 |
| 19 | $V_1P_{1.2}Sn_{0.3}O_{6.1}(SiO_2 70\%)$ | 94.5 | 80.3 | 85.0 |
| 20 | $V_1P_{1.2}Co_{0.3}O_{6.1}(SiO_2 70\%)$ | 97.4 | 85.5 | 87.8 |
| 21 | $V_1P_{1.2}Ni_{0.3}O_{6.1}(SiO_2 70\%)$ | 93.8 | 79.8 | 85.1 |

In Examples 16–21, catalysts were prepared in the similar manner as in Example 1 using chromium, manganese, iron, tin, cobalt or nickel nitrate.

In Example 15, catalyst was prepared in the similar manner as in Example 12 using chromium nitrate.

COMPARATIVE EXAMPLES 5 to 11

Examples 15 to 21 were repeated except that ethyl bromide was not used. The results are shown in Table 4.

TABLE 4

| Comparative Example | Catalyst | Conversion (%) | Yield (%) | Selectivity (%) |
|---|---|---|---|---|
| 5 | $V_1Cr_1O_{5.5}(\alpha\text{-}Al_2O_3 97\%)$ | 62.3 | 52.6 | 84.4 |
| 6 | $V_1P_{1.2}Cr_{0.3}O_{6.4}(SiO_2 70\%)$ | 70.0 | 55.4 | 79.1 |
| 7 | $V_1P_{1.2}Mn_{0.3}O_{6.55}(SiO_2 70\%)$ | 72.8 | 58.4 | 80.2 |
| 8 | $V_1P_{1.2}Fe_{0.3}O_{6.1}(SiO_2 70\%)$ | 67.9 | 50.7 | 74.7 |
| 9 | $V_1P_{1.2}Sn_{0.3}O_{6.1}(SiO_2 70\%)$ | 66.3 | 51.5 | 77.7 |
| 10 | $V_1P_{1.2}Co_{0.3}O_{6.1}(SiO_2 70\%)$ | 71.6 | 57.8 | 80.7 |
| 11 | $V_1P_{1.2}Ni_{0.3}O_{6.1}(SiO_2 70\%)$ | 68.4 | 50.3 | 73.5 |

What is claimed is:

1. A process for producing polychlorobenzonitrile having chlorine atoms at the 2,6-position by ammoxidation of toluene derivative having chlorine atoms at the 2,6-position with a gas containing ammonia and oxygen in vapour phase in the presence of a catalyst, characterized in that bromine and/or a bromine-containing compound is added to the reaction system.

2. A process according to claim 1 wherein the toluene derivative having chlorine atoms at the 2,6-position is 2,6-dichlorotoluene, 2,3,6-trichlorotoluene, or 2,4,6-trichlorotoluene.

3. A process according to claim 1 wherein the bromine-containing compound is one or more than one compound selected from hydrogen bromide, methyl bromide, dibromomethane, bromoform, carbon tetrabromide, ethyl bromide, 1,2-dibromomethane, n-propyl bromide, i-propyl bromide, n-butyl bromide, i-butyl bromide, sec-butyl bromide, i-amyl bromide, sec-amyl bromide, t-amyl bromide, cyclopentyl bromide, cyclohexyl bromide, bromobenzenes, and bromotoluenes.

4. A process according to claim 2 wherein the bromine-containing compound is ethyl bromide, n-propyl bromide, i-propyl bromide, or iso-amyl bromide.

5. A process according to claim 1, 3, or 4 wherein bromine and/or the bromine-containing compound is added in an amount of 0.1 to 10 wt % to the toluene derivative having chlorine atoms at the 2,6-position.

6. A process according to claim 2, 3, or 4 wherein the catalyst is one which has the following composition.

$$V_1P_aA_bO_c$$

wherein A denotes at least one element selected from the group consisting of chromium, manganese, iron, cobalt, nickel, and tin; and a, b, and c denote the atomic ratio of phosphorus, A, and oxygen, respectively, a being 0.5 to 3, b being 0 to 2, and c being a value which is determined according to the valence and atomic ratio of other elements.

7. A process according to claim 2, 3, or 4 wherein 2 to 5 mol each of oxygen and ammonia is used for 1 mol of the toluene derivative having chlorine atoms at the 2,6-position.

8. A process according to claim 1, 2, 3, or 4 wherein the reaction temperature is 330° to 450° C.

* * * * *